United States Patent [19]

Sumida et al.

[11] Patent Number: 5,801,277
[45] Date of Patent: Sep. 1, 1998

[54] SOLID CATALYST FOR ETHERIFICATION REACTION AND PRODUCTION PROCESS FOR ETHER COMPOUND USING THIS CATALYST

[75] Inventors: Yasutaka Sumida, Daito; Miaki Asakawa, Himeji; Yuichi Kita, Akashi; Mitsuhiro Kitajima, Suita; Yoshiyuki Takahashi, Kyoto; Kazuo Sagi, Suita, all of Japan

[73] Assignee: Nippon Shokubai Co., Ltd., Japan

[21] Appl. No.: 858,274

[22] Filed: May 19, 1997

[30] Foreign Application Priority Data

| May 23, 1996 | [JP] | Japan | 8-128335 |
| Aug. 28, 1996 | [JP] | Japan | 8-226298 |
| Nov. 11, 1996 | [JP] | Japan | 8-298997 |

[51] Int. Cl.$^6$ ................................ C07C 59/125
[52] U.S. Cl. .................. 562/583; 562/588; 562/587
[58] Field of Search ........................ 562/583, 588, 562/587

[56] References Cited

U.S. PATENT DOCUMENTS

| 4,061,594 | 12/1977 | Michel et al. |
| 4,118,420 | 10/1978 | Lannert |
| 4,152,295 | 5/1979 | Stapp |
| 5,057,627 | 10/1991 | Edwards |

FOREIGN PATENT DOCUMENTS

| 0 599 688 | 6/1994 | European Pat. Off. |
| WO 92/18449 | 10/1992 | WIPO |

OTHER PUBLICATIONS

Chemical Abstract 89458Z, Phosphorous-free detergent builders, vol. 75, p. 39, 1971.
Westrenen et al., Lanthanide (III)-catalysed Addition of Glycolate to Maleate: Investigation of Intermediates Using Multinuclear Magnetic Resonance Spectroscopy, J. Chem. Soc. Dalton Trans., 1988, pp. 2723-2728, Great Britain.

*Primary Examiner*—Gary Geist
*Assistant Examiner*—J. Parson

[57] ABSTRACT

The present invention provides: a solid catalyst which enables a person to simply and efficiently carry out an etherification reaction; and a process by which an ether compound is simply and efficiently produced using the solid catalyst. The solid catalyst is a first solid catalyst comprising at least one rare earth element, or is a second solid catalyst comprising a metallic compound which includes a metal atom and a nonmetal atom bonded to the metal atom, wherein the metallic compound has molecular orbitals including: at least one orbital (L) having an energy of $E_L$ (eV) which satisfies $E_{LUMO} \leq E_L \leq (E_{LUMO}+0.05)$ wherein $E_{LUMO}$ is an energy (eV) of the lowest unoccupied molecular orbital around the metal atom; and at least one orbital (H) having an energy of $E_H$ (eV) which satisfies $(E_{HOMO}-0.02) \leq E_H \leq E_{HOMO}$ wherein $E_{HOMO}$ is an energy (eV) of the highest occupied molecular orbital around the nonmetal atom; wherein at least one of orbitals (L) and at least one of orbitals (H) are both orientational. The process for producing an ether compound comprises the step of carrying out a reaction between an organic compound having a hydroxyl group and an unsaturated carboxylic acid compound or an epoxy compound in the presence of either or both of the first and the second solid catalyst, thus forming the ether compound.

14 Claims, No Drawings

5,801,277

SOLID CATALYST FOR ETHERIFICATION REACTION AND PRODUCTION PROCESS FOR ETHER COMPOUND USING THIS CATALYST

BACKGROUND OF THE INVENTION

A. Technical Field

The present invention relates to a solid catalyst for an etherification reaction and to a production process for an ether compound using this catalyst. More specifically, the invention relates to a solid catalyst which is easy to separate from a product system, and to a production process for an ether compound using this catalyst.

B. Background Art

It is known that biodegradable salts, particularly, sodium salts, of carboxymethoxysuccinic acid (CMOS) of the following formula:

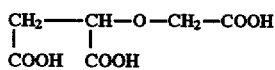

are useful as phosphorus-free detergent builders, and that these compounds are obtained by reacting maleic anhydride and glycolic acid (Chemical Abstract, 75, 89458 (1971)). This reaction is a homogeneous reaction using water-soluble calcium hydroxide (Ca (OH)$_2$) as a catalyst in an aqueous medium, and the resultant product is a calcium salt. Therefore, the following steps are needed: adding sodium carbonate (Na$_2$CO$_3$) after the completion of the reaction, thereby precipitating calcium carbonate (CaCO$_3$); and then filtering off the precipitated calcium carbonate from the objective sodium salts of CMOS. In addition, the above-cited literature teaches that calcium hydroxide can be replaced with hydroxides of zinc, strontium, barium, and magnesium.

Furthermore, it is reported that the calcium ion can be replaced with ions of lanthanoid elements as catalysts in the same homogeneous reaction as above-mentioned (J. Chem. Soc. Dalton Trans., 2723–2728 (1988)). In other words, it is taught that lanthanum salts of CMOS can be obtained by reacting sodium glycolate and disodium maleate in the presence of lanthanum trichloride (LaCl$_3$) in an aqueous medium. Therefore, it is necessary for obtaining the objective sodium salts of CMOS that the lanthanum ion is separated from the reaction products using ion-exchange resin or the like.

As above-mentioned, because the conventional processes involve homogeneous reactions, they need the step of separating the calcium ion, the lanthanum ion, or the like after the completion of the reactions. However, in the case where such a separating operation is carried out, the number of production steps increase to lead to the rise in the production cost. Therefore, in industrial practice, it is desirable to omit such a step regarding the separation of the catalyst as used.

The use of a solid catalyst is considered a solution to the above-mentioned inevitable problems in the conventional homogeneous reactions. However, the exploration of a new solid catalyst that is used for the production of an ether compound needed obtaining compounds of various chemical structures as solid catalysts and then actually carrying out experiments to examine the catalytic activity of the compounds, because relations between the catalytic activity and chemical structures of catalysts have not sufficiently been solved yet. Therefore it was complicated and very difficult to find a new solid catalyst of high catalytic activity from among many compounds.

Fukui et al.'s "Frontier Electron Theory" is famous as a means for predicting whether a chemical reaction advances or not. This is a theory that used molecular orbitals and thereby clarified which site in a molecule and how fast a chemical reaction of the molecule occurs, and at present, this theory is used for predicting various chemical reactions.

SUMMARY OF THE INVENTION

A. OBJECTS OF THE INVENTION

The present invention is directed to provide a solid catalyst which solves the above-mentioned inevitable problems in the conventional homogeneous reactions and thereby can produce ether compounds such as CMOS by a simple process involving no especial step regarding the catalyst separation, and to provide a production process for an ether compound using this catalyst, specifically, a process for producing a corresponding ether compound from an organic compound having a hydroxyl group and an unsaturated carboxylic acid compound or epoxy compound.

Accordingly, it is an object of the present invention to provide a solid catalyst which enables a person to simply and efficiently carry out an etherification reaction.

It is another object of the present invention to provide a solid catalyst which enables a person to carry out an etherification reaction in an aqueous medium with no especial step regarding the catalyst separation.

It is another object of the present invention to provide a solid catalyst of which the suitability for an etherification reaction can easily be known.

It is another object of the present invention to provide a process by which an ether compound is simply and efficiently produced using the solid catalyst.

B. DISCLOSURE OF THE INVENTION

The present inventors worked diligently to solve the above-mentioned problems and encountered some surprising solutions. As a result, they completed the present invention by finding that a catalyst comprising a rare earth element can be a solid catalyst which is suitable for an etherification reaction, and that if attention is paid to molecular orbitals of a catalyst, whether the catalyst has specificity as a catalyst for an etherification reaction or not can easily be known.

Thus, a solid catalyst for an etherification reaction, according to the present invention, comprises at least one rare earth element (hereinafter this catalyst is referred to as first solid catalyst).

Another solid catalyst for an etherification reaction, according to the present invention, comprises a metallic compound which includes a metal atom and a nonmetal atom bonded to the metal atom, wherein the metallic compound has molecular orbitals including:

at least one orbital (L) having an energy of $E_L$ (eV) which satisfies $E_{LUMO} \leq E_L \leq (E_{LUMO}+0.05)$ wherein $E_{LUMO}$ is an energy (eV) of the lowest unoccupied molecular orbital around the metal atom; and at least one orbital (H) having an energy of $E_H$ (eV) which satisfies $(E_{HOMO}-0.02) \leq E_H \leq E_{HOMO}$ wherein $E_{HOMO}$ is an energy (eV) of the highest occupied molecular orbital around the nonmetal atom;

wherein at least one of orbitals (L) and at least one of orbitals (H) are both orientational (hereinafter this catalyst is referred to as second solid catalyst).

A process for producing an ether compound, according to the present invention, comprises the step of carrying out a reaction between an organic compound having a hydroxyl group and an unsaturated carboxylic acid compound or an epoxy compound in the presence of at least one solid catalyst selected from the group consisting of the first and the second solid catalyst, thus forming the ether compound.

These and other objects and the advantages of the present invention will be more fully apparent from the following detailed disclosure.

DETAILED DESCRIPTION OF THE INVENTION

First, the first solid catalyst of the present invention is illustrated.

<First solid catalyst>

The first solid catalyst is a solid catalyst comprising at least one rare earth element. When needed, the first solid catalyst may further comprise other elements which do not damage effects of the present invention.

In the present invention, the rare earth element means lanthanoid elements, scandium, and yttrium. Typical examples of the lanthanoid elements are lanthanum, cerium, praseodymium, and neodymium, but, particularly, lanthanum is preferably used. Only one kind or two or more kinds of rare earth elements may be included in the first solid catalyst.

Specific examples of the first solid catalyst are as follows:

(a) a solid catalyst comprising at least one type selected from the group consisting of: a rare earth element oxide; a rare earth element phosphate; a rare earth element phosphonate; a rare earth element which is carried on a resin base having a phosphoric acid group; rare earth element hydroxide (I); a partially dehydrated product of hydroxide (I); compound (II) which is obtained by substituting at least one, but not all, of hydroxyl groups of hydroxide (I) with a corresponding number of phosphoric acid groups; and a partially dehydrated product of compound (II);

(b) a solid catalyst comprising at least one type selected from the group consisting of: a rare earth element oxide; a rare earth element phosphate; a rare earth element phosphonate; and a rare earth element which is carried on a resin base having a phosphoric acid group; and (c) a solid catalyst comprising at least one type selected from the group consisting of: rare earth element hydroxide (I); a partially dehydrated product of hydroxide (I); compound (II) which is obtained by substituting at least one, but not all, of hydroxyl groups of hydroxide (I) with a corresponding number of phosphoric acid groups; and a partially dehydrated product of compound (II).

The rare earth element oxide is commercially available, and such a commercially available one can be used in the present invention.

Typical examples of the rare earth element oxide are $Y_2O_3$, $La_2O_3$, $Nd_2O_3$, $Pm_2O_3$, $Sm_2O_3$, $Eu_2O_3$, $Ga_2O_3$, $Dy_2O_3$, $Ho_2O_3$, $Er_2O_3$, $Tm_2O_3$, $Yb_2O_3$, and $Lu_2O_3$.

The rare earth element phosphate, for example, can be prepared by processes as disclosed in the Bulletin of the Chemical Society of Japan, Vol. 51 (No. 12), pp. 3645–3646, published in 1978. Specifically, for example, cerium phosphate ($CePO_4$) can easily be obtained by reacting cerium trichloride with orthophosphoric acid or salts thereof (e.g. sodium dihydrogen phosphate) in an aqueous medium. Although this phosphate is usually obtained as a hydrate, any hydrate can be used in the present invention. The reaction temperature at which the above-mentioned reaction is carried out is not especially limited, and usually can adequately be selected from the range of about 20° to about 90° C. As to the ratio of the combination of the rare earth element chloride with orthophosphoric acid or salts thereof, the orthophosphoric acid or salts thereof are preferably used in a ratio of about 0.1 to about 3 mol, more preferably, about 0.2 to about 1.5 mol (particularly, where the rare earth element is lanthanum, preferably, about 1 to about 3 mol, more preferably, about 1 to about 1.5 mol), per mol of the rare earth element chloride. A solid rare earth element phosphate can be obtained by carrying out a reaction for a predetermined time under stirred conditions and then filtering the resultant precipitate. The phosphate, obtained in this way, can be used in any state of from a wet to dried one after filtered and washed. The rare earth element phosphate, as used in the present invention, does not need to have a purity of 100%, and even the rare earth element phosphate that is obtained as the precipitate in the above-mentioned reaction can be used as a solid catalyst without any especial purification step.

Typical examples of the rare earth element phosphate are $LaPO_4$, $YPO_4$, $CePO_4$, $PrPO_4$, $NdPO_4$, $PmPO_4$, $SmPO_4$, $EuPO_4$, $GdPO_4$, $TbPO_4$, $DyPO_4$, $HoPO_4$, $ErPO_4$, $TmPO_4$, $YbPO_4$, and $LuPO_4$.

The rare earth element phosphonate, for example, lanthanum phosphate, can be prepared in the same way as for the above-mentioned cerium phosphate except that cerium and phosphoric acid are replaced with lanthanum and phosphonic acid respectively. As to the ratio of the combination of the rare earth element chloride and phosphonic acid, the rare earth element chloride is preferably used in a ratio of about 0.5 to about 2.5 mol, more preferably, about 1 to about 2 mol, per mol of phosphonic acid. Similarly to the phosphate, the state of the phosphonate as used is not especially limited, and any state of from a wet to dried one can be used.

The solid catalyst comprising a rare earth element that is carried on a resin base having a phosphoric acid group, specifically, a resin base having either or both of a phosphonic group ($—PO_3H_2$) and a phosphinic group ($—PH_2O_2$) (in the present invention these resin bases are generically called a resin base having a phosphoric acid group), can be prepared, for example, by processes as disclosed in the Journal of the Applied Polymer Science, Vol. 52, pp. 1153–1164, published 1994. Typical examples of the resin base having a phosphoric acid group are as follows: resin (A) having the following repeating unit:

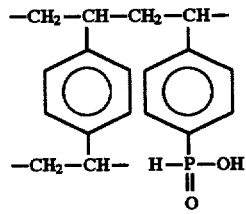

resin (B) having the following repeating unit:

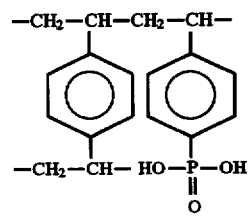

resin (C) having the following repeating unit:

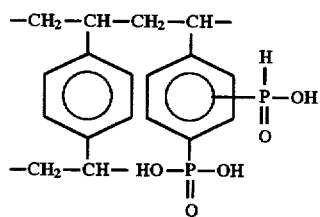

and resin (D) having the following repeating unit:

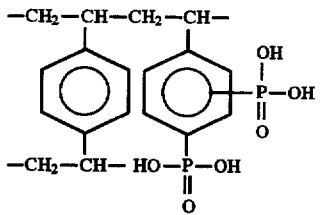

Any of these resins is a publicly known one that is disclosed in the above-mentioned literature, and they can be prepared as follows: styrene and divinylbenzene are used as starting materials and subjected to suspension polymerization in an organic solvent to produce resin (I), and this resin (I) and ether chloride are reacted in the presence of aluminum trichloride to produce resin (II), and this resin (II) is reacted with phosphorus trichloride in the presence of aluminum trichloride and then hydrolyzed to obtain resin (C), and this resin (C) is oxidized with nitric acid to obtain resin (D); or resin (I) is reacted with phosphorus trichloride in the presence of aluminum trichloride and then hydrolyzed to obtain resin (A), and this resin (A) is oxidized with nitric acid to obtain resin (B).

The crosslinking degree of the resin base can be adjusted by varying the ratio of divinyl benzene to styrene as used. In addition, the interstitial ratio of the resin base can be adjusted by adequately adding a foaming agent, such as 2,2,4-trimethylpentane, in the suspension polymerization of styrene and divinylbenzene.

The carriage of the rare earth element on the above-mentioned resins (A) to (D) can be made by bringing a rare earth element ion and the resin into contact with each other, specifically, by well-drying each of the above-mentioned resins, and then adding each of the well-dried resins to an aqueous solution of a rare earth element chloride, such as lanthanum trichloride, thus contacting them sufficiently, and then separating the resultant rare earth element as carried on the resin. In these steps, conditions such as the concentration of the rare earth element chloride and the contact temperature can adequately be determined depending on the desired amount of the carried rare earth element.

The preferable amount of the rare earth element as carried on each of the above-mentioned resins, depending on the crosslinking degree of the resin, is usually about 0.5 mmol or more per gram of the resin. The amount of the carried rare earth element can easily be determined by measuring the difference between the concentrations of the rare earth element ion in the aqueous solution thereof before and after the contact with the resin.

From a viewpoint of the catalytic activity, it is preferable that the first solid catalyst comprises at least one compound selected from the group consisting of: rare earth element hydroxide (I); a partially dehydrated product of hydroxide (I); compound (II) which is obtained by substituting at least one, but not all, of hydroxyl groups of hydroxide (I) with a corresponding number of phosphoric acid groups; and a partially dehydrated product of compound (II). This group of compounds can be denoted by a compositional formula, namely, the following general formula: $M(OH)_x(O)_y(PO_4)_z$ wherein: M is a rare earth element; $0<x\leq3$; $0\leq y<1.5$; $0\leq z<1$; and $x+2y+3z=3$.

In the present invention, it is important that x in the above-mentioned general formula is larger than zero, namely, that an —OH group is included in the compound, because the inclusion of an —OH group enhances the activity of the catalyst.

Rare earth element hydroxide (I) is a compound in the case where: x is 3, and y and z are both 0, in the aforementioned general formula. In other words, rare earth element hydroxide (I) is denoted by a compositional formula, $M(OH)_3$. $La(OH)_3$ is the most preferable of rare earth element hydroxides (I).

The production process for rare earth element hydroxide (I) is not especially limited, but rare earth element hydroxide (I), for example, can be produced by heating an aqueous solution of a rare earth element salt to about 20° to about 80° C. and then adding ammonia or an alkali to the heated solution to adjust the pH to about 10 or more, preferably, about 12 or more, thus precipitating a rare earth element hydroxide. Examples of the rare earth element salt are: halides such as chlorides, bromides and iodides; nitrates; and sulfates. Examples of the alkali are sodium hydroxide and potassium hydroxide. For example, $La(OH)_3$ can be produced as follows: sodium hydroxide is added to an aqueous solution of lanthanum chloride, as heated to about 50° C., until the pH increases to about 13 or more, and then the mixture is sufficiently stirred, thus obtaining a precipitate of $La(OH)_3$.

Compound (II), which is obtained by substituting at least one, but not all, of hydroxyl groups of hydroxide (I) with a corresponding number of phosphoric acid groups, is a compound in the case where $0<x<3$, $y=0$, and $0<z<1$ in the aforementioned general formula. In other words, compound (II) is represented by a compositional formula, $M(OH)_x(PO_4)_z$ (wherein $x+3z=3$), and can also be said to be a compound in which at least one, but not all, of phosphoric acid groups of a rare earth element phosphate is substituted with a corresponding number of —OH groups. A partial phosphate of a rare earth element hydroxide can inhibit the elution therefrom of the rare earth element in a wide pH region, and the activity of a partial hydroxide of a rare earth element phosphate is higher than that of an entire phosphate of a rare earth element, $(MPO_4)$. Of compounds (II), the most preferable one is a compound which is obtained by substituting at least one, but not all, of the hydroxyl groups of lanthanum hydroxide with a corresponding number of phosphoric acid groups. In compound (II), it is preferable that x and z fall in the ranges of $1.5<x<3$ and $0<z<0.5$ respectively, because compound (II) containing more hydroxyl groups has higher activity, and because the inclusion of the $PO_4$ group lowers the solubility of the catalyst.

The production process for compound (II) is not especially limited, but compound (II), for example, can be easily obtained by mixing a rare earth element salt with orthophosphoric acid or salts thereof (e.g. sodium dihydrogen phosphate) in a temperature range of about 20° to about 80° C. in an aqueous medium while the pH is maintained close at about 7, and then adjusting the pH to about 7.5 or more, preferably, about 8 or more, with ammonia or an alkali.

The orthophosphoric acid or salts thereof, as used in the above-exemplified production process for compound (II), have a phosphorus content of less than an equivalent mol of the rare earth element in the rare earth element salt. In this process, the molar ratio of the rare earth element to phosphorus in the resultant compound (II) is almost equal to that of the rare earth element in the starting rare earth element salt to phosphorus in the starting orthophosphoric acid or salts thereof. Accordingly, a rare earth element phosphate of optional composition can be obtained by adjusting the amount of the starting orthophosphoric acid or salts thereof as used relative to the rare earth element.

The rare earth element salt and the alkali, which are used in the above-exemplified production process for compound (II), may be the same as those used in the previously exemplified production process for compound (I). As to the phosphate, there can be exemplified sodium dihydrogen phosphate, disodium hydrogen phosphate, potassium dihydrogen phosphate, dipotassium hydrogen phosphate, ammonium dihydrogen phosphate, diammonium hydrogen phosphate, sodium phosphate, and potassium phosphate.

The partially dehydrated products of compounds (I) and (II) can be obtained by heating compounds (I) and (II) to partially dehydrate them, thus substituting at least one, but not all, of their hydroxyl groups with a corresponding number of (O). As to conditions in the thermal dehydration, a temperature of about 200° to about 800° C. and a duration of about 0.5 to about 10 hours are usually adequate. The partially dehydrated product of compound (I) is a compound in the case where x=3, 0<y<1.5, and 0<z<1 in the aforementioned general formula, and the partially dehydrated product of compound (II) is a compound in the case where 0<x<3, 0<y<1.5, and 0<z<1 in the aforementioned general formula. The inclusion of (O) due to the thermal dehydration improves the filtration easiness in the catalyst separation step after the etherification reaction. Of the partially dehydrated products of compounds (I) and (II), preferable ones are: a partially dehydrated product of La(OH)$_3$; and a partially dehydrated product of the compound which is obtained by substituting at least one, but not all, of the hydroxyl groups of lanthanum hydroxide with a corresponding number of phosphoric acid groups.

Next, the second solid catalyst is illustrated.

<Second solid catalyst>

The second solid catalyst is a catalyst comprising a metallic compound, and the metallic compound comprises a metal atom and a nonmetal atom that is bonded to the metal atom.

The metal atom is not especially limited, and may be any of the atoms that belong to groups 1A to 7A, group 8, and groups 1B to 7B in the long-form periodic table. Representative examples of the metal atom are rare earth elements. The meaning of the rare earth element for the second solid catalyst is the same as that of the rare earth element which is aforementioned with regard to the first solid catalyst, and preferable rare earth elements for the second solid catalyst are also the same as those mentioned previously as to the first solid catalyst.

The nonmetal atom is not especially limited if it is capable of bonding to the metal atom. Typical examples of the nonmetal atom are: halogen atoms such as a fluorine atom, a chlorine atom, a bromine atom, and an iodine atom; an oxygen atom; a sulfur atom; and a nitrogen atom.

The metallic compound has specific molecular orbitals and, as is below-mentioned in detail, it is defined from a result of molecular orbital calculation. The calculation of molecular orbitals is preferably carried out for the metallic compound itself. However, as to metallic compounds, such as YPO$_4$, Y$_2$O$_3$, and La$_2$O$_3$, having crystal structures in which structural units are not separated from each other, but are connected to each other to have linear or network structures, the calculation of molecular orbitals may be carried out by regarding as a metallic compound a partial structure that is cut out of a crystal structure including continuous repeating units or by regarding as a metallic compound a model structure that is formed by modifying a terminal of the above-mentioned partial structure with a hydrogen atom if need arises. For example, as to YPO$_4$, Y$_2$O$_3$, and La$_2$O$_3$, model structures shown in Table 4-2 are selected and regarded as metallic compounds, thus calculating molecular orbitals thereof. In addition, the calculation of molecular orbitals is carried out for the most stable structure of the metallic compound. The reason why the most stable structure is selected is because it is considered that when a catalyst and a reactant molecule approach each other in a transition state of a reaction, the energy changes with the change of their respective steric structures, but that the shapes of their molecular orbitals do not change basically. The most stable structure may be specified using jointly two or more calculation methods such as molecular mechanics and molecular dynamics.

The method for calculating molecular orbitals of the metallic compound is not especially limited, but is usually selected from empirical molecular orbital calculation, semiempirical molecular orbital calculation, and ab initio calculation. Particularly, the ab initio calculation is preferable, because if it is used for the calculation, the calculation precision is high and the calculation for many metallic compounds can be carried out. Examples of the ab initio calculation are Gaussian, HONDO, SPARTAN, and ADF. In addition, results of the molecular orbital calculation may be directly analyzed, but usually the results are converted into images of molecular orbitals utilizing visualization softwares such as Cerius2, Quanta, and InsightII.

The lowest unoccupied molecular orbital (LUMO) around the metal atom has an energy of $E_{LUMO}$ (eV) and is determined by molecular orbital calculation. Orbital (L) is at least one orbital that is located around the metal atom and has an energy of $E_L$ (eV) satisfying $E_{LUMO} \leq E_L \leq (E_{LUMO}+0.05)$. Orbitals having energies of not lower than $E_{LUMO}$ (e.g. LUMO, LUMO$^{+1}$, LUMO$^{+2}$, LUMO$^{+3}$, LUMO$^{+4}$, ...) are present around the metal atom, but, of these orbitals, orbital (L) is at least one of orbitals having energies in the range of $E_{LUMO}$ to $(E_{LUMO}+0.05)$ (eV). Orbital (L) is preferably at least one of orbitals having energies in the range of $E_{LUMO}$ to $(E_{LUMO}+0.02)$ (eV), because the difference between the energy of such orbital (L) around the metal atom and the energy of HOMO of the organic compound with an —OH group is small, and because the interaction between these orbitals is therefore large. Orbital (L) is not especially limited if it is located around the metal atom and has an energy in the above-mentioned range. However, orbital (L) is preferably LUMO, because the above-mentioned interaction becomes larger if orbital (L) is LUMO.

The highest occupied molecular orbital (HOMO) around the nonmetal atom has an energy of $E_{HOMO}$ (eV) and is determined by molecular orbital calculation. Orbital (H) is at least one orbital that is located around the nonmetal atom and has an energy of $E_H$ (eV) satisfying $(E_{HOMO}-0.02) \leq E_H \leq E_{HOMO}$. Orbitals having energies of not higher than $E_{HOMO}$ (e.g. HOMO, HOMO$^{-1}$, HOMO$^{-2}$, HOMO$^{-3}$, HOMO$^{-4}$, ...) are present around the nonmetal atom, but, of these orbitals, orbital (H) is at least one of orbitals having energies in the range of $(E_{HOMO}-0.02)$ to $E_{HOMO}$ (eV). Orbital (H) is preferably at least one of orbitals having energies in the range of $(E_{HOMO}-0.01)$ to $E_{HOMO}$ (eV), because the difference between the energy of such orbital (H) around the nonmetal atom and the energy of LUMO of the organic compound with an —OH group is small, and because the interaction between these orbitals is therefore large. Orbital (H) is not especially limited if it is located around the nonmetal atom and has an energy in the above-mentioned range. However, orbital (H) is preferably either or both of HOMO and $HOMO^{-1}$, because the above-mentioned interaction becomes larger if orbital (H) is such.

For example, as to the metallic compounds as exemplified in Table 4-1, molecular orbitals were calculated by a molecular orbital calculation software (GAUSSIAN94 (GAUSSIAN Inc.)) with HF method and LANL2DZ basis set. A visualization software (Cerius 2 (MSI)) was also used for this calculation. As a result, it was found that the metallic compounds satisfy the above-mentioned energy conditions, and that orbitals (H) and (L) are orbitals of energy values as enclosed on respective columns of the metallic compounds in Table 4-1.

As to the above-mentioned molecular orbitals of the metallic compound that is the essential component of the second solid catalyst, at least one of orbitals (L) and at least one of orbitals (H) are both orientational.

The orientational property that is referred to in the present invention is defined as follows: If orbital (L) around the metal atom is the shape of two or three lobes which center the metal atom, and if at least one discontinuous plane (nodal plane) is present between the lobes, and if a straight line that connects the respective centers of the lobes is present (hereinafter this straight line may be referred to as lobe straight line (L)), then orbital (L) is regarded as orientational. In addition, if orbital (H) around the nonmetal atom is the shape of two or three lobes which center the nonmetal atom, and if at least one discontinuous plane is present between the lobes, and if a straight line that connects the respective centers of the lobes is present (hereinafter this straight line may be referred to as lobe straight line (H)), then orbital (H) is regarded as orientational.

Herein, the center of the lobe, as mentioned above, means the center of gravity of the lobe when the lobe is assumed to be a homogenous substance.

Orbitals (L) and (H) preferably include at least one orbital, selected from the group consisting of p, d, and f orbitals, as the main constituent, because such orbitals are orientational. However, s orbitals are spherical and therefore are not orientational.

Of the metallic compounds as exemplified in Table 4-1, $YPO_4$ can, for example, be enumerated as an example of the metallic compound that is the essential component of the second solid catalyst. Hereinafter, $YPO_4$ is illustrated in detail.

As to $YPO_4$, orbitals (L) are LUMO, $LUMO^{+1}$, $LUMO^{+2}$, and $LUMO^{+3}$, and in addition, orbitals (H) are HOMO, $HOMO^{-1}$, $HOMO^{-2}$, and $HOMO^{-3}$.

Of these orbitals of $YPO_4$, LUMO and $HOMO^{-1}$ are shown in Table 4-2. LUMO of $YPO_4$ is distributed around the yttrium atom, and the main constituent of this LUMO is a d orbital, comprising two lobes, of the yttrium atom, and this d orbital is distributed in the shape of a dumbbell which centers the yttrium atom. In addition, a discontinuous plane is present between the lobes, and a straight line connecting the centers of the lobes is also present. Therefore, from the above-mentioned definition of the orientational property, LUMO of $YPO_4$ is orientational. On the other hand, $HOMO^{-1}$ of $YPO_4$ is distributed around the oxygen atom of the hydroxyl group, and the main constituent of this $HOMO^{-1}$ is a p orbital, comprising two lobes, of the oxygen atom, and this p orbital is distributed in the shape of a dumbbell which centers the oxygen atom. In addition, a discontinuous plane is present between the lobes, and a straight line connecting the centers of the lobes is also present. Therefore, from the above-mentioned definition of the orientational property, $HOMO^{-1}$ of $YPO_4$ is also orientational. Thus, LUMO and $HOMO^{-1}$ of $YPO_4$ are both orientational.

It is preferable that, of the molecular orbitals of the metallic compound as included in the second solid catalyst, at least one of orientational orbitals (L) has the same orientation as of at least one of orientational orbitals (H), because the catalytic activity is enhanced in such a case. Herein, the meaning of the same orientation in the present invention is as follows: when the metallic compound is arranged in three-dimensional space to draw its orbitals, and when lobe straight line (L) of at least one of orientational orbitals (L) and lobe straight line (H) of at least one of orientational orbitals (H) are parallelly transferred to arrange them to pass optional points in space, the angle, θ ($0° \leq θ \leq 90°$), of the resultant two straight lines to each other is about 45° or less, preferably, about 30° or less, more preferably, about 10° or less.

Next, the present invention process for producing an ether compound is illustrated.

<Production process for ether compound>

In the process of the present invention, a reaction between an organic compound having a hydroxyl group and an unsaturated carboxylic acid compound or an epoxy compound is carried out in the presence of either or both of the first and the second solid catalyst, whereby a corresponding ether compound can be produced efficiently without needing any further step, such as separation of the catalyst, after the reaction.

In this reaction, each of the first and the second solid catalyst may be used alone or in adequate combinations of two or more thereof.

The production of the ether compound is not especially limited if it is carried out in a heterogeneous system. For example, the production of the ether compound is carried out in heterogeneous systems such as in liquid phases (e.g. in aqueous media) or in gas phases. Herein, the liquid phase is a state where starting materials are homogeneously dissolved in an aqueous medium, and the heterogeneous system of the liquid phase is a state where a insoluble catalyst is present in the liquid phase.

The aqueous medium comprises water as the essential component, and may further comprise organic solvents, such as tetrahydrofuran, 1,2-dimethoxyethane, dimethylformamide, and hexamethylphosphoric triamide, if necessary.

Specific examples of the organic compound having a hydroxyl group are hydroxycarboxylic acid compounds, polyvalent alcohol compounds, higher alcohol compounds with 6 to 22 carbon atoms, and saccharides. These organic compounds are more specifically illustrated as follows:

(1) Hydroxycarboxylic acid compounds (a) Compounds of the following general formula (1):

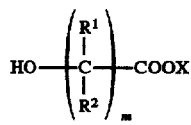

(1)

wherein: $R^1$ and $R^2$, independently of each other, denote a hydrogen atom or an alkyl with 1 to 3 carbon atoms; X denotes a hydrogen atom, an alkaline metal atom, an alkaline earth metal atom, an ammonium group, an alkylammonium group, or an alkanolammonium group; and m denotes an integer of 1 to 10. Typical examples are glycolic acid, β-hydroxypropionic acid, and lactic acid.

(b) Compounds of the following general formula (2):

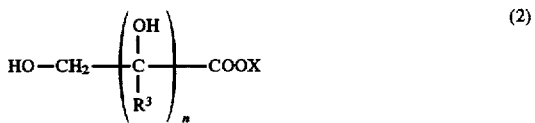

wherein: $R^3$ denotes a hydrogen atom or an alkyl with 1 to 3 carbon atoms; n denotes an integer of 1 to 10; and X is the same as that in general formula (1) above. Typical examples are glyceric acid and gluconic acid.

(c) Compounds of the following general formula (3):

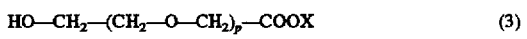

wherein: p denotes an integer of 1 to 10; and X is the same as that in general formula (1) above. Typical examples are diethylene glycol monocarboxylates.

(d) Compounds of the following general formula (4):

wherein: $R^4$ and $R^5$, independently of each other, denote a hydrogen atom or an alkyl with 1 to 3 carbon atoms; $R^6$ denotes a hydrogen atom, an alkyl with 1 to 8 carbon atoms, or hydroxyl; and X is the same as that in general formula (1) above. Typical examples are malic acid and tartaric acid.

(e) Compounds of the following general formula (5):

wherein: $R^7$ denotes a hydrogen atom or an alkyl with 1 to 3 carbon atoms; and X is the same as that in general formula (1) above. A typical example is tartronic acid.

(f) Compounds of the following general formula (6):

wherein: $R^8$, $R^9$, $R^{10}$, and $R^{11}$, independently of each other, denote a hydrogen atom or an alkyl with 1 to 3 carbon atoms; and X is the same as that in general formula (1) above. A typical example is citric acid.

(2) Polyvalent alcohol compounds (a) Compounds of the following general formula (7):

wherein $R^{12}$ to $R^{15}$, independently of each other, denote a hydrogen atom or an alkyl with 1 to 3 carbon atoms. Typical examples are ethylene glycol and isopropylene glycol.

(b) Products by condensation of 2 to 10 molecules of compounds of general formula (7) above:

A typical example thereof is diethylene glycol.

(c) Glycerol and derivatives therefrom:

Typical examples thereof are glycerol, diglycerol, and polyglycerol.

(d) Sorbitol, 1,4-sorbitan, pentaerythritol, dipentaerythritol.

(3) Higher alcohol compounds with 6 to 22 carbon atoms (R—OH)

Typical examples thereof are alcohols in which R is hexyl, heptyl, octyl, nonyl, decyl, undecyl, lauryl, myristyl, palmityl, stearyl, arachidyl, behenyl, oleyl, linol, linolenyl, or 2-ethylhexyl.

(4) Saccharides

Typical examples thereof are glucose, mannose, galactose, fructose, lactose, and sucrose.

Specific examples of the aforementioned unsaturated carboxylic acid compounds are unsaturated monocarboxylic acids and unsaturated dicarboxylic acids. These are more specifically illustrated as follows:

(1) Unsaturated monocarboxylic acid compounds (a) Compounds of the following general formula (8):

wherein: $R^{16}$ to $R^{18}$, independently of each other, denote a hydrogen atom or an alkyl with 1 to 10 carbon atoms; and X is the same as that in general formula (1) above. Typical examples are acrylic acid and methacrylic acid.

(2) Unsaturated dicarboxylic acid compounds (a) Compounds of the following general formula (9):

wherein: $R^{19}$ and $R^{20}$, independently of each other, denote a hydrogen atom or an alkyl with 1 to 10 carbon atoms; and X is the same as that in general formula (1) above. A typical example is maleic acid. The unsaturated dicarboxylic acid may be an anhydrous one.

In addition, specific examples of the aforementioned epoxy compounds are the following compounds:

(1) Compounds of the following general formula (10)

wherein: $R^{21}$ to $R^{24}$, independently of each other, denote a hydrogen atom, an alkyl with 1 to 10 carbon atoms, or —(CH$_2$)$_n$—COOX (wherein: n is an integer of 0 to 10; and X is the same as that in general formula (1) above); and at least one of $R^{21}$ to $R^{24}$ is —(CH$_2$)$_n$—COOX. Typical examples are glycidic acid and epoxysuccinic acid.

Accordingly, in a preferable embodiment of the present invention, compound (A) is reacted with compound (B) or epoxy compound (C) in the presence of the solid catalyst of the present invention, thus producing a corresponding ether compound, wherein: compound (A) is at least one compound selected from the group consisting of hydroxycarboxylic acids (e.g. glycolic acid, β-hydroxypropionic acid, lactic acid, glyceric acid, gluconic acid, diethylene glycol monocarboxylic acids, malic acid, tartaric acid, tartronic acid, citric acid), polyvalent alcohols (e.g. ethylene glycol, isopropylene glycol, diethylene glycol, glycerol, diglycerol, polyglycerol, sorbitol, 1,4-sorbitan, pentaerythritol, dipentaerythritol), higher alcohols with 6 to 22 carbon atoms, and saccharides (e.g. glucose, mannose, galactose, fructose, lactose, sucrose); compound (B) is at least one compound selected from the group consisting of unsaturated monocarboxylic acids (e.g. acrylic acid, methacrylic acid)

and unsaturated dicarboxylic acids (e.g. (anhydrous) maleic acid); and epoxy compound (C) is at least one compound selected from the group consisting of glycidic acid and epoxysuccinic acid. In a particularly preferable embodiment, glycolic acid, malic acid, tartaric acid, or tartronic acid, selected from compounds (A) above, is reacted with (anhydrous) maleic acid, selected from compounds (B) above, or with epoxysuccinic acid, selected from compounds (C) above, thus producing a corresponding ether compound.

An equation of the reaction between (A) the organic compound having a hydroxyl group and (B) the unsaturated carboxylic acid compound or (C) the epoxy compound is illustrated below when (A), (B), and (C) are glycolic acid, maleic acid, and epoxysuccinic acid respectively:

Reaction between glycolic acid and maleic acid:

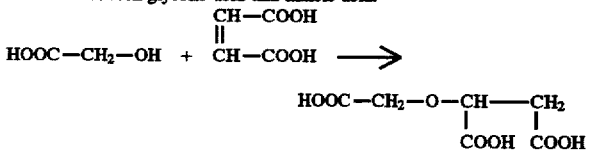

Reaction between glycolic acid and epoxysuccinic acid:

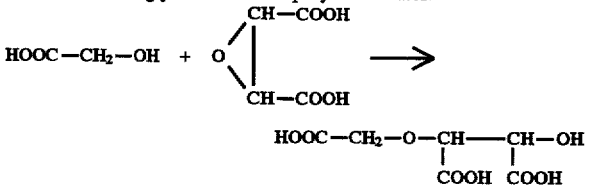

The production process of the present invention is usually carried out at a temperature in a range of about 40° to about 150° C., preferably, about 70° to about 120° C., for example, when carried out in an aqueous medium. The reaction pressure may be either a normal or increased one, but the reaction is usually carried out under normal pressure. The ratio of (A) the organic compound having a hydroxyl group to (B) the unsaturated carboxylic acid compound or (C) the epoxy compound is usually in a range of about 0.5 to about 2, preferably, about 0.8 to about 1.2, in terms of molar ratio of (A)/(B) or (A)/(C). The amount of the solid catalyst, as used, can adequately be selected from the ranges of, usually, about 0.1 to about 5 mol, preferably, about 0.5 to about 2 mol, per mol of (A) the organic compound having a hydroxyl group.

When (A) the organic compound having a hydroxyl group and (B) the unsaturated carboxylic acid compound are reacted with each other, for example, in an aqueous medium, in accordance with the production process of the present invention, they are preferably reacted in the form of alkaline metal salts, particularly, sodium salts, of at least one, more preferably all, of carboxyl groups in each of compounds (A) and (B). Specifically, when glycolic acid and maleic anhydride are reacted with each other to produce CMOS, they are preferably reacted as sodium glycolate and disodium maleate respectively. Although an aqueous solution of trisodium salt of CMOS (CMOS-3Na) is obtained as a product, either this aqueous solution itself or a solid as obtained by distilling off water from this solution may be used depending on the usage thereof. In addition, the reaction may be carried out under conditions where the reaction solution is alkalized, specifically, where the pH of the reaction solution is adjusted to, usually, about 7.5 or more, preferably, the range of about 7.5 to about 13. In this adjustment of the pH, sodium hydroxide is particularly preferably used.

Furthermore, similarly to the above-mentioned reaction, when (A) the organic compound having a hydroxyl group and (C) the epoxy compound are reacted with each other in an aqueous medium, they are also preferably reacted in the form of alkaline metal salts, particularly, sodium salts, of at least one, more preferably all, of carboxyl groups in each of compounds (A) and (C). Specifically, when glycolic acid and epoxysuccinic acid are reacted with each other to produce carboxymethoxymalic acid (CMOM), they are preferably reacted as sodium glycolate and disodium epoxysuccinate respectively. Although an aqueous solution of trisodium salt of CMOM (CMOM-3Na) is obtained as a product, either this aqueous solution itself or a solid as obtained by distilling off water from this solution may be used depending on the usage thereof. In addition, similarly to the aforementioned reaction, this reaction also may be carried out under conditions where the reaction solution is alkalized, specifically, where the pH of the reaction solution is adjusted to, usually, about 7.5 or more, preferably, the range of about 7.5 to about 10.5. In this adjustment of the pH, sodium hydroxide is particularly preferably used.

When the process of the present invention is carried out in an aqueous medium, the manner of the reaction may be either a continuous or batch manner. However, especially, if the reaction is carried out in a continuous manner, the objective ether compound can be produced with high productivity.

Of the ether compounds as obtained by the process of the present invention, CMOS, CMOM, and alkaline metal salts, particularly, sodium salts, thereof have biodegradability and further have excellent metal ion scavangeability, and therefore are useful as detergent builders.

When the solid catalyst of the present invention and the organic compound having a hydroxyl group are, for example, YPO$_4$ and sodium glycolate respectively, the reaction mechanism by which the ether compound is formed using the solid catalyst is considered as follows: as is shown by the below-mentioned formula, YPO$_4$ and sodium glycolate first interact upon each other to form intermediate (I), and then the activated oxygen atom of the hydroxyl group of sodium glycolate attacks at the unsaturated bond to form the ether compound. In this reaction mechanism, the step in which intermediate (I) is formed is the most important.

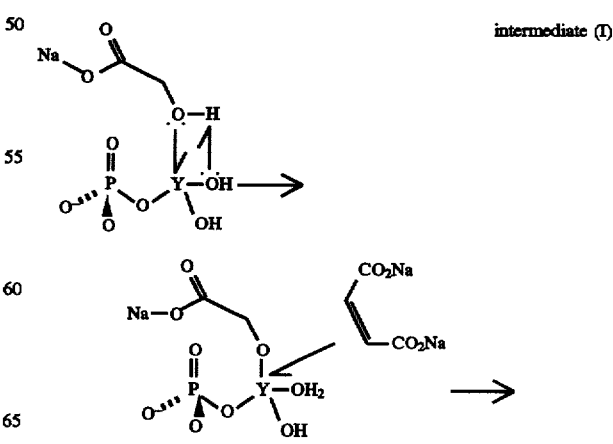

intermediate (I)

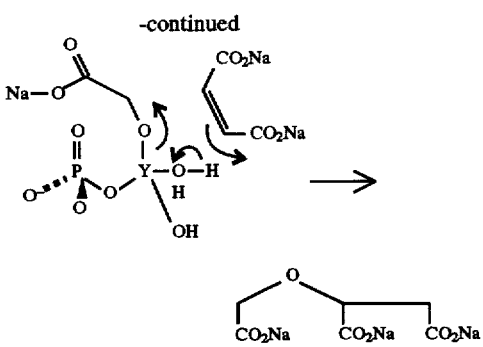

The below-mentioned formula shows a transition state in which intermediate (I) above is formed. Because LUMO of the yttrium atom and HOMO$^{-1}$ of the oxygen atom, as bonded to the yttrium atom, are both orientational, an interaction between the catalyst and the hydroxyl group of sodium glycolate occurs to thereby form intermediate (I). However, unless both of LUMO and HOMO$^{-1}$ are orientational, no interaction between the catalyst and the hydroxyl group of sodium glycolate occurs, so no intermediate (I) is formed and therefore no ether compound that is the final product is obtained. In addition, it is considered that because the orientations of LUMO and HOMO$^{-1}$ in intermediate (I) are the same as each other, (a) an inflow of electrons from HOMO around the oxygen atom in the hydroxyl group of sodium glycolate to LUMO around the yttrium atom and (b) an inflow of electrons from HOMO$^{-1}$ around the oxygen atom, as bonded to the yttrium atom, to LUMO around the hydrogen atom in the hydroxyl group of sodium glycolate occur easily, whereby the reaction advances smoothly.

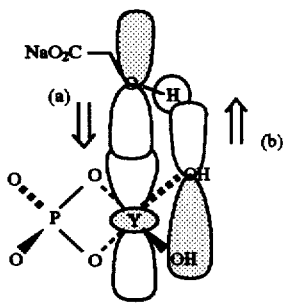

(Effects and advantages of the invention)

If either or both of the first and the second solid catalyst of the present invention are used, a heterogeneous reaction can be carried out in place of conventional homogeneous reactions. Therefore, the catalyst is easy to separate after the reaction, so the reaction steps can be simplified. Thus, the catalyst enables a person to simply and efficiently carry out etherification reactions, particularly, that in an aqueous medium.

Particularly, the second solid catalyst of the present invention is defined by its molecular orbitals, so its catalytic activity does not need to be examined by complicated experiments, and thus, whether the catalyst is suitable for the etherification reaction or not can easily be known.

In the present invention process for producing an ether compound, because a heterogeneous reaction between an organic compound having a hydroxyl group and an unsaturated carboxylic acid compound or an epoxy compound is carried out in the presence of either or both of the above-mentioned first and second solid catalysts in place of conventional homogeneous reactions, a corresponding ether compound can simply and efficiently be produced.

DETAILED DESCRIPTION OF THE PREFERRED EMBODIMENTS

Hereinafter, the present invention is illustrated by the following examples of some preferred embodiments in comparison with comparative examples not according to the invention. However, the present invention is not limited to these examples.

EXAMPLE 1-1

(Preparation of lanthanum phosphate)

First, 74.2 g of lanthanum chloride heptahydrate was dissolved into 200 g of water, and then 71.6 g of disodium hydrogen phosphate dodecahydrate was added, and the pH of the resultant solution was adjusted close to 9 with a 48 wt % aqueous sodium hydroxide solution. Then the reaction was carried out at 50° C. for 1 hour. After the reaction had finished, the resultant precipitate was filtered off, washed with water several times, and then dried under reduced pressure, whereby a white solid was obtained in a yield of 53.4 g. From X-rays diffraction analysis of this solid product, it was confirmed that this product had a structure of lanthanum phosphate.

(Etherification reaction)

First, 9.8 g of maleic anhydride was dissolved into 200 g of water, and then 7.6 g of glycolic acid was added, and furthermore 12.0 g of sodium hydroxide was added. To the resultant solution, 26.7 g of the above-obtained lanthanum phosphate was added, and then the reaction was carried out at 90° C. for 24 hours under stirred conditions. After the reaction had finished, the reaction solution was filtered, and the filtrate was analyzed by HPLC (high performance liquid chromatography). As a result, it was found that trisodium carboxymethoxysuccinate (CMOS-3Na) was obtained in a yield of 40.6 mol % (based on maleic anhydride). In addition, a white crystal, as obtained by drying off and solidifying the above-mentioned filtrate by evaporation, was analyzed by $^1$H-NMR and $^{13}$C-NMR. As a result, it was confirmed that the main component of the white crystal was CMOS-3Na.

Furthermore, the filtrate was analyzed by ICP (inductively coupled plasma) emission spectrometry, which showed that the concentration of the lanthanum ion in the filtrate was 0.5 ppm or less.

EXAMPLE 2-1

(Preparation of cerium phosphate)

First, 149.06 g of cerium chloride heptahydrate was dissolved into 200 g of water, and then 143.2 g of disodium hydrogen phosphate dodecahydrate was added, and the pH of the resultant solution was adjusted close to 9 with a 48 wt % aqueous sodium hydroxide solution. Then the reaction was carried out at 50° C. for 1 hour. After the reaction had finished, the resultant precipitate was filtered off, washed with water several times, and then dried under reduced pressure, whereby a white solid was obtained in a yield of 110.2 g. From X-rays diffraction analysis of this solid product, it was confirmed that this product had a structure of cerium phosphate.

(Etherification reaction)

First, 9.8 g of maleic anhydride was dissolved into 200 g of water, and then 7.6 g of glycolic acid was added, and furthermore 12.0 g of sodium hydroxide was added. To the resultant solution, 27.6 g of the above-obtained cerium phosphate was added, and then the pH was adjusted close to 10. Then the reaction was carried out at 90° C. for 24 hours under stirred conditions. After the reaction had finished, the reaction solution was filtered, and the filtrate was analyzed by HPLC (high performance liquid chromatography). As a result, it was found that trisodium carboxymethoxysuccinate (CMOS-3Na) was obtained in a yield of 34.5 mol % (based on maleic anhydride). In addition, a white crystal, as obtained by drying off and solidifying the above-mentioned filtrate by evaporation, was analyzed by $^1$H-NMR and $^{13}$C-NMR. As a result, it was confirmed that the main component of the white crystal was CMOS-3Na.

Furthermore, the filtrate was analyzed by ICP (inductively coupled plasma) emission spectrometry, which showed that the concentration of the cerium ion in the filtrate was 0.5 ppm or less.

EXAMPLE 2-2
(Preparation of yttrium phosphate)

A reaction was carried out in the same way as in the preparation of cerium phosphate in Example 2-1 except that cerium chloride heptahydrate was replaced with yttrium chloride hexahydrate. As a result, yttrium phosphate was obtained in a yield of 92.8 g.
(Etherification reaction)

An etherification reaction was carried out in the same way as of Example 2-1 except that 27.6 g of cerium phosphate was replaced with 23.2 g of yttrium phosphate as obtained above, and that the reaction duration was changed to 12 hours. As a result, CMOS-3Na was obtained in a yield of 12 mol %.

Furthermore, the filtrate was analyzed in the same way as of Example 2-1. As a result, the concentration of the yttrium ion in the filtrate was 0.1 ppm or less.

EXAMPLES 2-3A TO 2-3C

An etherification reaction was carried out using lanthanum oxide, neodymium oxide, and yttrium oxide, which were all commercially available, as rare earth element oxides as follows:

An etherification reaction was carried out in the same way as of Example 2-1 except that cerium phosphate was replaced with lanthanum oxide, neodymium oxide, and yttrium oxide, and that the reaction duration was changed to 12 hours. The amount of the addition of each oxide and the product yield therefrom are shown in Table 2-1.

Furthermore, the filtrate was analyzed in the same way as of Example 2-1. As a result, the respective concentrations of the metal ions in the filtrates in the use of the metal oxides were 0.5 ppm or less for the lanthanum ion, 0.5 ppm or less for the neodymium ion, and 0.5 ppm or less for the yttrium ion.

TABLE 2-1

| Example | Solid catalyst | Amount of addition (g) | Yield (mol %) |
|---------|----------------|------------------------|---------------|
| 2-3A | Lanthanum oxide | 32.6 | 30.8 |
| 2-3B | Neodymium oxide | 33.6 | 20.3 |
| 2-3C | Yttrium oxide | 22.6 | 14.5 |

EXAMPLE 2-4

First, 9.8 g of maleic anhydride was dissolved into 200 g of water, and then 15.0 g of tartaric acid was added, and furthermore 16.0 g of sodium hydroxide was added. To the resultant solution, 27.6 g of cerium phosphate as obtained in Example 2-1 was added, and then the pH was adjusted close to 10. Then the reaction was carried out at 90° C. for 24 hours under stirred conditions. After the reaction had finished, the reaction solution was filtered, and the filtrate was analyzed by HPLC (high performance liquid chromatography). As a result, it was found that tetrasodium tartrate monosuccinate (TMS-4Na) was obtained in a yield of 16.4 mol % (based on maleic anhydride). In addition, a white crystal, as obtained by drying off and solidifying the above-mentioned filtrate by evaporation, was analyzed by $^1$H-NMR and $^{13}$C-NMR. As a result, it was confirmed that the white crystal contained TMS-4Na.

Furthermore, the filtrate was analyzed in the same way as of Example 2-1. As a result, the concentration of the cerium ion in the filtrate was 1 ppm or less.

EXAMPLES 2-5A TO 2-5C

An etherification reaction was carried out in the same way as of Example 2-4 except that cerium phosphate was replaced with yttrium phosphate, as obtained in Example 2-2, and with lanthanum oxide and neodymium oxide, which were both commercially available. The amount of the addition of each of yttrium phosphate, lanthanum oxide, and neodymium oxide and the product yield therefrom are shown in Table 2-2.

Furthermore, the filtrate was analyzed in the same way as of Example 2-1. As a result, the respective concentrations of the metal ions in the filtrates were 1 ppm or less for the yttrium ion, 1 ppm or less for the lanthanum ion, and 1 ppm or less for the neodymium ion.

TABLE 2-2

| Example | Solid catalyst | Amount of addition (g) | Yield (mol %) |
|---------|----------------|------------------------|---------------|
| 2-5A | Yttrium phosphate | 23.2 | 15.9 |
| 2-5B | Lanthanum oxide | 32.6 | 18.6 |
| 2-5C | Neodymium oxide | 33.6 | 17.0 |

EXAMPLE 3-1
(Preparation of lanthanum hydroxide)

First, 148.4 g of lanthanum chloride heptahydrate was dissolved into 500 g of water, and then a 48 wt % aqueous sodium hydroxide solution was added until the pH increased to 13 or more. Then the mixture was stirred for 5 hours and then allowed to stand stationary over one night. The resultant precipitate was filtered off, washed with water several times, and then dried at 90° C. under reduced pressure for 2 hours, whereby a white solid was obtained in a yield of 95.6 g. From X-rays diffraction analysis of this solid product, it was confirmed that this product had a structure of lanthanum hydroxide (La(OH)$_3$).
(Etherification reaction)

First, 9.8 g of maleic anhydride was dissolved into 200 g of water, and then 7.6 g of glycolic acid was added, and furthermore 12.0 g of sodium hydroxide was added. To the resultant solution, 23.9 g of the above-obtained lanthanum hydroxide was added, and then the pH was adjusted close to 12.5. Then the reaction was carried out at 90° C. for 12 hours under stirred conditions. After the reaction had finished, the reaction solution was filtered, and the filtrate was analyzed by HPLC (high performance liquid chromatography). As a result, it was found that trisodium carboxymethoxysuccinate (CMOS-3Na) was obtained in a yield of 39.6 mol % (based on maleic anhydride). In addition, a white crystal, as obtained by drying off and solidifying the above-mentioned filtrate by evaporation, was analyzed by $^1$H-NMR and $^{13}$C-NMR. As a result, it was confirmed that the main component of the white crystal was CMOS-3Na.

Furthermore, the filtrate was analyzed by ICP (inductively coupled plasma) emission spectrometry, which showed that the concentration of the lanthanum ion in the filtrate was in a range of 1 to 10 ppm.

EXAMPLE 3-2

An etherification reaction was carried out in the same way as of Example 3-1 except that 23.9 g of lanthanum hydroxide was replaced with a product as obtained by treating 23.9 g of lanthanum hydroxide at 300° C. for 5 hours (in this product, at least one, but not all, of the hydroxyl groups of lanthanum hydroxide was substituted with a corresponding number of (O) by partial dehydration). After the reaction had finished, the filtrate was analyzed in the same way as of Example 3-1. As a result, it was found that CMOS-3Na was obtained in a yield of 41.8 mol % (based on maleic anhydride), and that the main component of the filtrate was CMOS-3Na, and that the concentration of the lanthanum ion in the filtrate was in a range of 1 to 10 ppm.

EXAMPLE 3-3

An etherification reaction was carried out in the same way as of Example 3-1 except that 23.9 g of lanthanum hydroxide was replaced with a product as obtained by treating 23.9 g of lanthanum hydroxide at 500° C. for 5 hours (in this product, at least one, but not all, of the hydroxyl groups of lanthanum hydroxide was substituted with a corresponding number of (O) by partial dehydration). After the reaction had finished, the filtrate was analyzed in the same way as of Example 3-1. As a result, it was found that CMOS-3Na was obtained in a yield of 40.3 mol % (based on maleic anhydride), and that the main component of the filtrate was CMOS-3Na, and that the concentration of the lanthanum ion in the filtrate was 1 ppm or less.

EXAMPLE 3-4

(Preparation of phosphate)

First, 74.2 g of lanthanum chloride heptahydrate was dissolved into 200 g of water, and then 53.7 g of disodium hydrogen phosphate dodecahydrate was added. The pH of the resultant solution was adjusted to 8 with a 48 wt % aqueous sodium hydroxide solution, and then the mixture was stirred at 50° C. for 1 hour. Then the resultant precipitate was filtered off, washed with water several times, and then dried at 90° C, under reduced pressure for 2 hours, whereby white solid (P-1), La(OH)$_x$(PO$_4$)$_z$ wherein x+3z=3, 0<x<3, 0<z<1, was obtained in a yield of 76.0 g. This solid was analyzed. As a result, the La/P ratio by mol was 1.34.

(Etherification reaction)

First, 9.8 g of maleic anhydride was dissolved into 200 g of water, and then 7.6 g of glycolic acid was added, and furthermore 12.0 g of sodium hydroxide was added. To the resultant solution, 38.0 g of the above-obtained solid (P-1) was added, and then the pH was adjusted close to 12.5. Then the reaction was carried out at 90° C. for 12 hours under stirred conditions. After the reaction had finished, the filtrate was analyzed in the same way as of Example 3-1. As a result, it was found that CMOS-3Na that the main component of the filtrate was CMOS-3Na, and that the concentration of the lanthanum ion in the filtrate was 1 ppm or less.

EXAMPLE 3-5

A reaction was carried out in the same way as of the preparation of phosphate in Example 3-4 except that the amount of disodium hydrogen phosphate dodecahydrate, as used, was changed to 35.8 g. Thereby white solid (P-2), La(OH)$_x$(PO$_4$)$_z$ wherein x+3z=3, 0<x<3, 0<z<1, was obtained in a yield of 52.8 g. This solid was analyzed. As a result, the La/P ratio by mol was 2.01.

An etherification reaction was carried out in the same way as of Example 3-4 except that 38.0 g of (P-1) was replaced with 26.4 g of (P-2). After the reaction had finished, the filtrate was analyzed in the same way as of Example 3-1. As a result, it was found that CMOS-3Na was obtained in a yield of 29.4 mol % (based on maleic anhydride), and that the main component of the filtrate was CMOS-3Na, and that the concentration of the lanthanum ion in the filtrate was in a range of 1 to 10 ppm.

EXAMPLE 3-6

An etherification reaction was carried out in the same way as of Example 3-5 except that 26.4 g of (P-2) was replaced with a product as obtained by treating 26.4 g of (P-2) at 300° C. for 5 hours (in this product, at least one, but not all, of hydroxyl groups of (P-2) was substituted with a corresponding number of (O) by partial dehydration). After the reaction had finished, the filtrate was analyzed in the same way as of Example 3-1. As a result, it was found that CMOS-3Na was obtained in a yield of 30.4 mol % (based on maleic anhydride), and that the main component of the filtrate was CMOS-3Na, and that the concentration of the lanthanum ion in the filtrate was 1 ppm or less.

EXAMPLE 3-7

A reaction was carried out in the same way as of the preparation of phosphate in Example 3-5 except that the pH was adjusted close to 10. Thereby white solid (P-3), La(OH)$_x$(PO$_4$)$_z$ wherein x+3z=3, 0<x<3, 0<z<1, was obtained in a yield of 58.1 g. This solid was analyzed. As a result, the La/P ratio by mol was 2.14.

An etherification reaction was carried out in the same way as of Example 3-4 except that 38.0 g of (P-1) was replaced with 29.0 g of (P-3), and that the pH was adjusted close to 10. After the reaction had finished, the filtrate was analyzed in the same way as of Example 3-1. As a result, it was found that CMOS-3Na was obtained in a yield of 33.1 mol % (based on maleic anhydride), and that the main component of the filtrate was CMOS-3Na, and that the concentration of the lanthanum ion in the filtrate was 1 ppm or less.

EXAMPLE 3-8

An etherification reaction was carried out in the same way as of Example 3-7 except that 29.0 g of (P-3) was replaced with a product as obtained by treating 29.0 g of (P-3) at 300° C. for 5 hours (in this product, at least one, but not all, of hydroxyl groups of (P-3) was substituted with a corresponding number of (O) by partial dehydration). After the reaction had finished, the filtrate was analyzed in the same way as of Example 3-1. As a result, it was found that CMOS-3Na was obtained in a yield of 42.4 mol % (based on maleic anhydride), and that the main component of the filtrate was CMOS-3Na, and that the concentration of the lanthanum ion in the filtrate was 1 ppm or less.

EXAMPLE 3-9

A reaction was carried out in the same way as of the preparation of phosphate in Example 3-4 except that the amount of disodium hydrogen phosphate dodecahydrate, as used, was changed to 21.5 g. Thereby white solid (P-4), La(OH)$_x$(PO$_4$)$_z$ wherein x+3z=3, 0<x<3, 0<z<1, was obtained in a yield of 44.1 g. This solid was analyzed. As a result, the La/P ratio by mol was 3.30.

An etherification reaction was carried out in the same way as of Example 3-4 except that 38.0 g of (P-1) was replaced with 44.1 g of (P-4). After the reaction had finished, the filtrate was analyzed in the same way as of Example 3-1. As a result, it was found that CMOS-3Na was obtained in a yield of 37.5 mol % (based on maleic anhydride), and that the main component of the filtrate was CMOS-3Na, and that the concentration of the lanthanum ion in the filtrate was in a range of 10 to 50 ppm.

EXAMPLE 3-10

An etherification reaction was carried out in the same way as of Example 3-9 except that 44.1 g of (P-4) was replaced with a product as obtained by treating 44.1 g of (P-4) at 300° C. for 5 hours (in this product, at least one, but not all, of hydroxyl groups of (P-4) was substituted with a corresponding number of (O) by partial dehydration). After the reaction had finished, the filtrate was analyzed in the same way as of Example 3-1. As a result, it was found that CMOS-3Na was obtained in a yield of 39.8 mol % (based on maleic anhydride), and that the main component of the filtrate was CMOS-3Na, and that the concentration of the lanthanum ion in the filtrate was in a range of 10 to 50 ppm.

EXAMPLE 3-11

A reaction was carried out in the same way as of the preparation of phosphate in Example 3-4 except that the pH was adjusted close to 10. Thereby white solid (P-5), La(OH)$_x$(PO$_4$)$_z$ wherein x+3z=3, 0<x<3, 0<z<1, was obtained in a yield of 78.6 g. This solid was analyzed. As a result, the La/P ratio by mol was 3.42.

An etherification reaction was carried out in the same way as of Example 3-4 except that 38.0 g of (P-1) was replaced with 39.3 g of (P-5), and that the pH was adjusted close to 10. After the reaction had finished, the filtrate was analyzed in the same way as of Example 3-1. As a result, it was found that CMOS-3Na was obtained in a yield of 44.2 mol % (based on maleic anhydride), and that the main component of the filtrate was CMOS-3Na, and that the concentration of the lanthanum ion in the filtrate was 1 ppm or less.

EXAMPLE 3-12

A reaction was carried out in the same way as of the preparation of phosphate in Example 3-4 except that the pH was adjusted close to 12. Thereby white solid (P-6), La(OH)$_x$(PO$_4$)$_z$ wherein x+3z=3, 0<x<3, 0<z<1, was obtained in a yield of 85.6 g. This solid was analyzed. As a result, the La/P ratio by mol was 3.46.

An etherification reaction was carried out in the same way as of Example 3-4 except that 38.0 g of (P-1) was replaced with a product as obtained by treating 42.8 g of (P-6) at 300° C. for 5 hours (in this product, at least one, but not all, of hydroxyl groups of (P-6) was substituted with a corresponding number of (O) by partial dehydration), and that the pH was adjusted close to 12. After the reaction had finished, the filtrate was analyzed in the same way as of Example 3-1. As a result, it was found that CMOS-3Na was obtained in a yield of 45.3 mol % (based on maleic anhydride), and that the main component of the filtrate was CMOS-3Na, and that the concentration of the lanthanum ion in the filtrate was 1 ppm or less.

The data about Examples 3-4 to 3-12 are collectively shown in Table 3-1.

TABLE 3-1

| | Preparation of phosphate | | | | | Etherification reaction | | | |
|---|---|---|---|---|---|---|---|---|---|
| Example | NaH$_2$PO$_4$·12H$_2$O | pH | Amount of white solid | La/P | Phosphate | Amount of catalyst | pH | Yield (mol %) | La$^{3+}$ concentration |
| 3-4 | 53.7 g | 8 | 76.0 g | 1.34 | P-1 | 38.0 g | 12.5 | 25.5 | <1 ppm |
| 3-5 | 35.8 g | 8 | 52.8 g | 2.01 | P-2 | 26.4 g | 12.5 | 29.4 | 1–50 ppm |
| 3-6 | | | | | | 26.4 g heated* | 12.5 | 30.4 | <1 ppm |
| 3-7 | 35.8 g | 10 | 58.1 g | 2.14 | P-3 | 29.0 g | 10 | 33.1 | <1 ppm |
| 3-8 | | | | | | 29.0 g heated* | 10 | 42.4 | <1 ppm |
| 3-9 | 21.5 g | 8 | 44.1 g | 3.30 | P-4 | 44.1 g | 12.5 | 37.5 | 10–50 ppm |
| 3-10 | | | | | | 44.1 g heated* | 12.5 | 39.8 | 10–50 ppm |
| 3-11 | 21.5 g | 10 | 78.6 g | 3.42 | P-5 | 39.3 g | 10 | 44.2 | <1 ppm |
| 3-12 | 21.5 g | 12 | 85.6 g | 3.46 | P-6 | 42.8 g heated* | 12 | 45.3 | <1 ppm |

*: The heating of the phosphate was all carried out at 300° C. for 5 hours.

EXAMPLE 3-13

An etherification reaction was carried out in the same way as of Example 3-4 except that 38.0 g of (P-1) was replaced with 27.6 of cerium phosphate, as obtained in Example 2-1, and that the pH was adjusted close to 10. After the reaction had finished, the filtrate was analyzed in the same way as of Example 3-1. As a result, it was found that CMOS-3Na was obtained in a yield of 20.6 mol % (based on maleic anhydride), and that the main component of the filtrate was CMOS-3Na, and that the concentration of the cerium ion in the filtrate was 0.5 ppm or less.

EXAMPLE 3-14

First, 9.8 g of sodium glycolate and 38.0 g of the above-obtained solid (P-1) were added to 64.7 g of a 30 wt % aqueous disodium epoxysuccinate solution, and then the pH was adjusted so as to fall in the range of 8.5 to 9. Then the reaction was carried out at 90° C. for 8 hours under stirred conditions. After the reaction had finished, the filtrate was analyzed in the same way as of Example 3-1. As a result, it was found that trisodium carboxymethoxymalate (CMOM-3Na) was obtained in a yield of 10.2 mol % (based on disodium epoxysuccinate), and that the concentration of the lanthanum ion in the filtrate was 1 ppm or less.

EXAMPLE 4-1

(Example of molecular orbital calculation for lanthanum oxide)

As to the model structure of lanthanum oxide as shown in Table 4-2, molecular orbitals were calculated by a molecular orbital calculation software (GAUSSIAN94 (GAUSSIAN Inc.)) with HF method and LANL2DZ basis set. A visualization software (Cerius 2 (MSI)) was also used for this calculation. Results of the calculation are shown in Table 4-1. Of the orbitals of lanthanum oxide, LUMO and $HOMO^{-1}$ are shown in Table 4-2. LUMO of lanthanum oxide is distributed around the lanthanum atom, and the main constituent of this LUMO is a d orbital, comprising two lobes, of the lanthanum atom, and this d orbital is distributed in the shape of a dumbbell which centers the lanthanum atom. In addition, a discontinuous plane is present between the lobes, and a straight line connecting the centers of the lobes is also present. Therefore, from the definition of the orientational property, LUMO of lanthanum oxide is orientational. On the other hand, $HOMO^{-1}$ of lanthanum oxide is distributed around the oxygen atom, and the main constituent of this $HOMO^{-1}$ is a p orbital, comprising two lobes, of the oxygen atom, and this p orbital is distributed in the shape of a dumbbell which centers the oxygen atom. In addition, a discontinuous plane is present between the lobes, and a straight line connecting the centers of the lobes is also present. Therefore, from the definition of the orientational property, $HOMO^{-1}$ of lanthanum oxide is also orientational. Thus, LUMO and $HOMO^{-1}$ of lanthanum oxide are both orientational.

In addition, the angle between LUMO and $HOMO^{-1}$ was measured as about 0°.

EXAMPLE 4-2

(Example of molecular orbital calculation for yttrium oxide)

As to the model structure of yttrium oxide as shown in Table 4-2, molecular orbitals were calculated utilizing the same molecular orbital calculation and visualization softwares as in Example 4-1. Results of the calculation are shown in Table 4-1. Of the orbitals of yttrium oxide, LUMO and $HOMO^{-1}$ are shown in Table 4-2. LUMO of yttrium oxide is distributed around the yttrium atom, and the main constituent of this LUMO is a d orbital, comprising two lobes, of the yttrium atom, and this d orbital is distributed in the shape of a dumbbell which centers the yttrium atom. In addition, a discontinuous plane is present between the lobes, and a straight line connecting the centers of the lobes is also present. Therefore, from the definition of the orientational property, LUMO of yttrium oxide is orientational. On the other hand, $HOMO^{-1}$ of yttrium oxide is distributed around the oxygen atom, and the main constituent of this $HOMO^{-1}$ is a p orbital, comprising two lobes, of the oxygen atom, and this p orbital is distributed in the shape of a dumbbell which centers the oxygen atom. In addition, a discontinuous plane is present between the lobes, and a straight line connecting the centers of the lobes is also present. Therefore, from the definition of the orientational property, $HOMO^{-1}$ of yttrium oxide is also orientational. Thus, LUMO and $HOMO^{-1}$ of yttrium oxide are both orientational.

EXAMPLE 4-3

(Example of molecular orbital calculation for yttrium phosphate)

As to the model structure of yttrium phosphate as shown in Table 4-2, molecular orbitals were calculated utilizing the same molecular orbital calculation and visualization softwares as in Example 4-1. Results of the calculation are shown in Table 4-1. Of the orbitals of yttrium phosphate, LUMO and $HOMO^{-1}$ are shown in Table 4-2. LUMO of yttrium phosphate is distributed around the yttrium atom, and the main constituent of this LUMO is a d orbital, comprising two lobes, of the yttrium atom, and this d orbital is distributed in the shape of a dumbbell which centers the yttrium atom. In addition, a discontinuous plane is present between the lobes, and a straight line connecting the centers of the lobes is also present. Therefore, from the definition of the orientational property, LUMO of yttrium phosphate is orientational. On the other hand, $HOMO^{-1}$ of yttrium phosphate is distributed around the oxygen atom of the hydroxyl group, and the main constituent of this $HOMO^{-1}$ is a p orbital, comprising two lobes, of the oxygen atom, and this p orbital is distributed in the shape of a dumbbell which centers the oxygen atom. In addition, a discontinuous plane is present between the lobes, and a straight line connecting the centers of the lobes is also present. Therefore, from the definition of the orientational property, $HOMO^{-1}$ of yttrium phosphate is also orientational. Thus, LUMO and $HOMO^{-1}$ of yttrium phosphate are both orientational.

EXAMPLE 4-4

(Example of lanthanum oxychloride)
(Molecular orbital calculation)

As to the model structure of lanthanum oxychloride as shown in 4-2, molecular orbitals were calculated utilizing the same molecular orbital calculation and visualization softwares as in Example 4-1. Results of the calculation are shown in Table 4-1. Of the orbitals of lanthanum oxychloride, LUMO and $HOMO^{-1}$ are shown in Table 4-2. LUMO of lanthanum oxychloride is distributed around the lanthanum atom, and the main constituent of this LUMO is a d orbital, comprising two lobes, of the lanthanum atom, and this d orbital is distributed in the shape of a dumbbell which centers the lanthanum atom. In addition, a discontinuous plane is present between the lobes, and a straight line connecting the centers of the lobes is also present. Therefore, from the definition of the orientational property, LUMO of lanthanum oxychloride is orientational. On the other hand, $HOMO^{-1}$ of lanthanum oxychloride is distributed around the chlorine atom, and the main constituent of this $HOMO^{-1}$ is a p orbital, comprising two lobes, of the chlorine atom, and this p orbital is distributed in the shape of a dumbbell which centers the chlorine atom. In addition, a discontinuous plane is present between the lobes, and a straight line connecting the centers of the lobes is also present. Therefore, from the definition of the orientational property, $HOMO^{-1}$ of lanthanum oxychloride is also orientational. Thus, LUMO and $HOMO^{-1}$ of lanthanum oxychloride are both orientational.

(Preparation of lanthanum oxychloride)

A white solid was obtained in a yield of 47.4 g by heating 92.8 g of lanthanum chloride hydrate at 600° C. for 24 hours. From X-rays diffraction analysis of this white solid, it was confirmed that this solid had a structure of lanthanum oxychloride.

(Etherification reaction)

An etherification reaction was carried out in the same way as of Example 2-1 except that cerium phosphate was replaced with 23.7 g of lanthanum oxychloride as obtained above, and that the reaction duration was changed to 12 hours. After the reaction had finished, the reaction solution was filtered, and the filtrate was analyzed by HPLC (high performance liquid chromatography). As a result, it was found that trisodium carboxymethoxysuccinate (CMOS-3Na) was obtained in a yield of 35.8 mol % (based on maleic anhydride). In addition, a white crystal, as obtained by drying off and solidifying the above-mentioned filtrate by evaporation, was analyzed by $^1$H-NMR and $^{13}$C-NMR. As a result, it was confirmed that the main component of the white crystal was CMOS-3Na.

Furthermore, the filtrate was analyzed by ICP (inductively coupled plasma) emission spectrometry, which showed that the concentration of the lanthanum ion in the filtrate was 0.5 ppm or less.

Comparative Example 4-1

(Calcium phosphate and magnesium phosphate as comparative examples)
(Molecular orbital calculation)

As to the model structure of calcium phosphate as shown in Table 4-2, molecular orbitals were calculated utilizing the same molecular orbital calculation and visualization softwares as in Example 4-1. Results of the calculation are shown in Table 4-1. LUMO and HOMO of the model structure of calcium phosphate are shown in Table 4-2. HOMO of calcium phosphate is distributed around the oxygen atom of the hydroxyl group, and the main constituent of this HOMO is a p orbital, comprising two lobes, of the oxygen atom, and this p orbital is distributed in the shape of a dumbbell which centers the oxygen atom. In addition, a discontinuous plane is present between the lobes, and a straight line connecting the centers of the lobes is also present. Therefore, from the definition of the orientational property, HOMO of calcium phosphate is orientational. However, as to LUMO of calcium phosphate, it is distributed around the calcium atom, but its main constituent is an s orbital, so LUMO of calcium phosphate is not orientational. Therefore, calcium phosphate cannot be used as a solid catalyst for an etherification reaction.

Similarly to calcium phosphate, LUMO of magnesium phosphate is distributed around the magnesium atom, but the main constituent of this LUMO is also an s orbital, so LUMO of magnesium phosphate is not orientational, either. Therefore, magnesium phosphate cannot be used as a solid catalyst for an etherification reaction, either.
(Etherification reaction)

An etherification reaction was carried out in the same way as of Example 2-1 except that cerium phosphate, as used as a catalyst, was replaced with calcium phosphate, and that the reaction duration was changed to 12 hours. However, trisodium carboxymethoxysuccinate (CMOS-3Na) was not obtained. In addition, an etherification reaction was carried out in which the catalyst was replaced with magnesium phosphate. However, CMOS-3Na was not obtained, either.

Comparative Example 4-2

(Iron phosphate as comparative example)
(Molecular orbital calculation)

As to the model structure of iron phosphate as shown in Table 4-2, molecular orbitals were calculated utilizing the same molecular orbital calculation and visualization softwares as in Example 4-1. Results of the calculation are shown in Table 4-1. LUMO and HOMO of the model structure of iron phosphate are shown in Table 4-2.

HOMO of iron phosphate is distributed around the oxygen atom of the phosphoric acid group, and the main constituent of this HOMO is a p orbital, comprising two lobes, of the oxygen atom, and this p orbital is distributed in the shape of a dumbbell which centers the oxygen atom. In addition, a discontinuous plane is present between the lobes, and a straight line connecting the centers of the lobes is also present. Therefore, from the definition of the orientational property, HOMO of iron phosphate is orientational. On the other hand, LUMO of iron phosphate is distributed around the iron atom, and the main constituent of this LUMO is a d orbital, comprising four lobes, of the iron atom, and is not an orbital, comprising two or three lobes, of the iron atom. Therefore, from the definition of the orientational property, LUMO of iron phosphate is not orientational. Thus iron phosphate cannot be used as a solid catalyst for an etherification reaction.

(Etherification reaction)

An etherification reaction was carried out in the same way as of Example 2-1 except that cerium phosphate, as used as a catalyst, was replaced with iron phosphate, and that the reaction duration was changed to 12 hours. However, iron phosphate decomposed, so trisodium carboxymethoxysuccinate (CMOS-3Na) was not obtained.

Comparative Example 4-3

(Aluminum phosphate as comparative example)

(Molecular orbital calculation)

As to the model structure of aluminum phosphate as shown in Table 4-2, molecular orbitals were calculated utilizing the same molecular orbital calculation and visualization softwares as in Example 4-1. Results of the calculation are shown in Table 4-1. LUMO and HOMO of the model structure of aluminum phosphate are shown in Table 4-2.

HOMO of aluminum phosphate is distributed around the oxygen atom of the hydroxyl group, and the main constituent of this HOMO is a p orbital, comprising two lobes, of the oxygen atom, and this p orbital is distributed in the shape of a dumbbell which centers the oxygen atom. In addition, a discontinuous plane is present between the lobes, and a straight line connecting the centers of the lobes is also present. Therefore, from the definition of the orientational property, HOMO of aluminum phosphate is orientational. On the other hand, LUMO of aluminum phosphate is distributed around the aluminum atom, and the main constituent of this LUMO is an s orbital of the aluminum atom, so there is no discontinuous plane. Therefore, from the definition of the orientational property, LUMO of aluminum phosphate is not orientational. Thus aluminum phosphate cannot be used as a solid catalyst for an etherification reaction.

(Etherification reaction)

An etherification reaction was carried out in the same way as of Example 2-1 except that cerium phosphate, as used as a catalyst, was replaced with aluminum phosphate, and that the reaction duration was changed to 12 hours. However, trisodium carboxymethoxysuccinate (CMOS-3Na) was not obtained.

TABLE 4-1

| | YPO$_4$ | La$_2$O$_3$ | Y$_2$O$_3$ | LaOCl |
|---|---|---|---|---|
| LUMO$^{+6}$ | — | 0.0662 | — | — |
| LUMO$^{+5}$ | — | 0.0572 | — | — |
| LUMO$^{+4}$ | 0.1435 | 0.0508 | — | — |
| LUMO$^{+3}$ | 0.0750 | 0.0506 | 0.0655 | 0.0308 |
| LUMO$^{+2}$ | 0.0667 | 0.0454 | 0.0520 | −0.0140 |
| LUMO$^{+1}$ | 0.0628 | 0.0086 | 0.0167 | −0.0210 |
| LUMO | 0.0585 | 0.0069 | 0.0080 | −0.3977 |
| HOMO | −0.4531 | −0.3556 | −0.3787 | −0.3989 |
| HOMO$^{-1}$ | −0.4544 | −0.3648 | −0.3859 | −0.3992 |
| HOMO$^{-2}$ | −0.4638 | −0.3730 | −0.4099 | −0.4000 |
| HOMO$^{-3}$ | −0.4647 | −0.3812 | — | −0.4080 |
| HOMO$^{-4}$ | −0.4808 | — | — | −0.4151 |
| HOMO$^{-5}$ | — | — | — | −0.4162 |
| HOMO$^{-6}$ | — | — | — | −0.4277 |
| HOMO$^{-7}$ | — | — | — | — |

| | CaPO$_4$ | MgPO$_4$ | FePO$_4$ | AlPO$_4$ |
|---|---|---|---|---|
| LUMO$^{+4}$ | 0.1808 | — | 0.1829 | — |
| LUMO$^{+3}$ | 0.0896 | 0.1374 | 0.0895 | — |
| LUMO$^{+2}$ | 0.0704 | 0.1042 | 0.0728 | — |
| LUMO$^{+1}$ | 0.0524 | 0.0921 | 0.0643 | 0.1640 |
| LUMO | 0.0513 | 0.0672 | 0.0576 | 0.1077 |
| HOMO | −0.3903 | −0.4463 | −0.4885 | −0.4723 |
| HOMO$^{-1}$ | −0.3908 | −0.4465 | −0.4927 | −0.4773 |
| HOMO$^{-2}$ | −0.4649 | −0.4776 | −0.4927 | −0.4896 |
| HOMO$^{-3}$ | — | — | −0.5005 | −0.5008 |
| HOMO$^{-4}$ | — | — | −0.5075 | — |
| HOMO$^{-5}$ | — | — | −0.5117 | — |

(unit: eV)

TABLE 4-2

| Catalyst | LUMO | HOMO or HOMO$^{-1}$ | Reaction (experimental fact) |
|---|---|---|---|
| YPO$_4$ | | | advanced |
| M$_2$O$_3$ M = La, Y | | | advanced |
| LaOCl | | | advanced |

TABLE 4-2-continued

| Catalyst | LUMO | HOMO or HOMO⁻¹ | Reaction (experimental fact) |
|---|---|---|---|
| MPO₄ M = Ca, Mg | | | not advanced |
| FePO₄ | | | not advanced (catalyst decomposed) |
| AlPO₄ | | | not advanced |

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A process for producing an ether compound, which comprises the step of carrying out a reaction between an organic compound having a hydroxyl group and an unsaturated carboxylic acid compound in the presence of at least one solid catalyst selected from the group consisting of a first and a second solid catalyst, thus forming the ether compound, wherein:

the first solid catalyst includes a rare earth element; and the second solid catalyst includes a metallic compound which includes a metal atom and a nonmetal atom bonded to the metal atom, wherein the metallic compound has molecular orbitals including:

at least one orbital (L) having an energy of $E_L$ (eV) which satisfies $E_{LUMO} \leq E_L \leq (E_{LUMO}+0.05)$ wherein $E_{LUMO}$ is an energy (eV) of the lowest unoccupied molecular orbital around the metal atom; and at least one orbital (H) having an energy of $E_H$ (eV) which satisfies $(E_{HOMO}-0.02) \leq E_H \leq E_{HOMO}$ wherein $E_{HOMO}$ is an energy (eV) of the highest occupied molecular orbital around the nonmetal atom;

wherein at least one of orbitals (L) and at least one of orbitals (H) are both orientational.

2. A process according to claim 1, wherein the reaction is carried out in an aqueous medium.

3. A process according to claim 1, wherein: the organic compound having a hydroxyl group is at least one compound selected from the group consisting of glycolic acid, malic acid, tartaric acid, tartronic acid, and alkaline metal salts thereof; and the unsaturated carboxylic acid compound is at least one compound selected from the group consisting of maleic acid, maleic anhydride, and alkaline metal salts thereof.

4. A process according to claim 1, wherein the first solid catalyst comprises at least one type selected from the group consisting of: a rare earth element oxide; a rare earth element phosphate; a rare earth element phosphonate; a rare earth element which is carried on a resin base having a phosphoric acid group; rare earth element hydroxide (I); a partially dehydrated product of hydroxide (I); compound (II) which is obtained by substituting at least one, but not all, of hydroxyl groups of hydroxide (I) with a corresponding number of phosphoric acid groups; and a partially dehydrated product of compound (II).

5. A process according to claim 4, wherein the rare earth element in the first solid catalyst is lanthanum.

6. A process according to claim 5, wherein the first solid catalyst is lanthanum phosphate.

7. A process according to claim 5, wherein the first solid catalyst comprises a compound which is obtained by substituting at least one, but not all, of hydroxyl groups of lanthanum hydroxide with a corresponding number of phosphoric acid groups.

8. A process for producing an ether compound, which comprises the step of caring out a reaction between an organic compound having a hydroxyl group and an epoxy compound in the presence of at least one solid catalyst selected from the group consisting of a first and a second solid catalyst, thus forming the ether compound, wherein:

the first solid catalyst includes a rare earth element; and the second solid catalyst includes a metallic compound which includes a metal atom and a nonmetal atom bonded to the metal atom, wherein the metallic compound has molecular orbitals including:

at least one orbital (L) having an energy of $E_L$ (eV) which satisfies $E_{LUMO} \leq E_L \leq (E_{LUMO}+0.05)$ wherein $E_{LUMO}$ is an energy (eV) of the lowest unoccupied molecular orbital around the metal atom; and at least one orbital (H) having an energy of $E_H$ (eV) which satisfies $(E_{HOMO}-0.02) \leq E_H \leq E_{HOMO}$ wherein $E_{HOMO}$ is an energy (eV) of the highest occupied molecular orbital around the nonmetal atom;

wherein at least one of orbitals (L) and at least one of orbitals (H) are both orientational.

9. A process according to claim 8, wherein the reaction is carried out in an aqueous medium.

10. A process according to claim 8, wherein: the organic compound having a hydroxyl group is at least one compound selected from the group consisting of glycolic acid, malic acid, tartaric acid, tartronic acid, and alkaline metal salts thereof; and the epoxy compound is at least one compound selected from the group consisting of epoxysuccinic acid and alkaline metal salts thereof.

11. A process according to claim 8, wherein the first solid catalyst comprises at least one type selected from the group consisting of: a rare earth element oxide; a rare earth element phosphate; a rare earth element phosphonate; a rare earth element which is carried on a resin base having a phosphoric acid group; rare earth element hydroxide (I); a partially dehydrated product of hydroxide (I); compound (II) which is obtained by substituting at least one, but not all, of hydroxyl groups of hydroxide (I) with a corresponding number of phosphoric acid groups; and a partially dehydrated product of compound (II).

12. A process according to claim 11, wherein the rare earth element in the first solid catalyst is lanthanum.

13. A process according to claim 12, wherein the first solid catalyst is lanthanum phosphate.

14. A process according to claim 12, wherein the first solid catalyst comprises a compound which is obtained by substituting at least one, but not all, of hydroxyl groups of lanthanum hydroxide with a corresponding number of phosphoric acid groups.

* * * * *